(12) United States Patent
Igarashi (10) Patent No.: US 9,476,821 B2
(45) Date of Patent: Oct. 25, 2016

(54) PLUG GAUGE WITH MAINTENANCE LINE AND ROUND POINT AND METHOD OF MANUFACTURING THE SAME

(71) Applicant: NIIGATA SEIKI CO., LTD., Tokyo (JP)

(72) Inventor: Toshiyuki Igarashi, Tokyo (JP)

(73) Assignee: NIIGATA SEIKI CO., LTD., Tokyo (JP)

( * ) Notice: Subject to any disclaimer, the term of this patent is extended or adjusted under 35 U.S.C. 154(b) by 328 days.

(21) Appl. No.: 14/170,332

(22) Filed: Jan. 31, 2014

(65) Prior Publication Data
US 2014/0299042 A1 Oct. 9, 2014

(30) Foreign Application Priority Data
Apr. 3, 2013 (JP) ................... 2013-077350

(51) Int. Cl.
| | |
|---|---|
| *G01N 19/00* | (2006.01) |
| *C25D 5/02* | (2006.01) |
| *C25D 7/00* | (2006.01) |
| *G01B 3/50* | (2006.01) |
| *C25D 17/14* | (2006.01) |
| *G01N 3/56* | (2006.01) |

(52) U.S. Cl.
CPC ............... *G01N 19/00* (2013.01); *C25D 5/022* (2013.01); *C25D 5/026* (2013.01); *C25D 7/00* (2013.01); *C25D 17/14* (2013.01); *G01B 3/50* (2013.01); *G01N 3/56* (2013.01); *G01N 2203/0664* (2013.01)

(58) Field of Classification Search
CPC ....................................................... G01B 3/50

USPC ......................................... 116/208; 33/501.45
See application file for complete search history.

(56) References Cited

U.S. PATENT DOCUMENTS

| | | | | |
|---|---|---|---|---|
| 5,131,158 A | * | 7/1992 | Wong | G01B 3/50 33/501.45 |
| 5,388,331 A | * | 2/1995 | Doroodian-Shoja Siamak | B26B 21/4087 116/208 |
| 2012/0132129 A1 | * | 5/2012 | Edmond | B64D 45/00 116/208 |

FOREIGN PATENT DOCUMENTS

| | | | | |
|---|---|---|---|---|
| GB | 2061512 A | * | 5/1981 | ............... G01B 3/50 |
| JP | 2001-116502 A | | 4/2001 | |
| JP | 2006-177908 A | | 7/2006 | |

\* cited by examiner

*Primary Examiner* — Daniel S Larkin
*Assistant Examiner* — Irving A Campbell
(74) *Attorney, Agent, or Firm* — Holtz, Holtz & Volek PC (57) ABSTRACT

Due to repeated use of a gauge portion, used to perform positioning and accuracy comparison measurement at the time of manufacture of various type of molds for metal-working, a gauge line on an outer circumferential surface portion of the gauge portion can disappear due to friction. A plug gauge body, which helps a user recognize the time for maintenance and replacement of the plug gauge, has a constricted portion formed on one side of a shank portion and a cylindrical gauge portion having a uniform diameter and extending from one side of the constricted portion, with the shank portion, the constricted portion, and the gauge portion, being formed axially, a wear checking gauge line having a predetermined depth and width formed so as to extend from one end portion of an outer circumferential surface portion of the gauge portion in the direction of the constricted portion.

8 Claims, 6 Drawing Sheets

PLUG GAUGE WITH MAINTENANCE LINE AND ROUND POINT AND METHOD OF MANUFACTURING THE SAME

FIELD OF THE INVENTION

The present invention relates to a plug gauge with a maintenance line and a round point which has a wear checking gauge line and round point, each having a predetermined depth and width, formed on the outer circumferential surface portion of a cylindrical gauge portion which forms the plug gauge body and has a uniform diameter, and can quickly and reliably inform the time for maintenance of the gauge portion, and a method of manufacturing the same.

DESCRIPTION OF THE RELATED ART

Conventionally, Japanese Patent Laid-Open No. 2006-177908 discloses a plug gauge having constricted portions formed coaxially with a disclosed handle on the left and right two sides of the handle and including a go-side measuring portion and a not-go-side measuring portion on the extensions of the constricted portions.

The outer circumferential surface portions of gauge portions 11 and 12 formed by extending the end portions of the constricted portions formed on the left and right two sides of the handle of the plug gauge have undergone nothing but the formation of DLC coating films each formed by an amorphous structure containing carbon as a main component.

In addition, conventionally, Japanese Patent Laid-Open No. 2001-116502 discloses a hole plug gauge.

Although air pressure ventilation passages are provided in the outer circumferential surfaces of gauge portions 2 formed by extending the end portions of connecting portions 5 formed on the left and right two sides of a shaft member 1 which forms the hole plug gauge, no wear checking gauge line is formed on the gauge.

CITATION LIST

Patent Literature

[Patent Literature 1] Japanese Patent Laid-Open No. 2006-177908

[Patent Literature 2] Japanese Patent Laid-Open No. 2001-116502

SUMMARY OF THE INVENTION

Problem that the Invention is to Solve

The conventional cylindrical plug gauge disclosed in Japanese Patent Laid-Open No. 2006-177908 is configured such that the gauge portions 11 and 12 are coaxially coupled to a handle 13, and a DLC coating film 20 formed from an amorphous structure containing carbon as a main component is formed on each of the surfaces of the gauge portions 11 and 12.

An object of the plug gauge is to maintain measurement accuracy by reducing the frictional force acting on the slidable contact portion of the plug gauge by means of the smooth DLC coating film formed on the surface of the gauge portion when the gauge portion is inserted into a hole to be measured and suppressing wear of the gauge portion even if the gauge portion is repeatedly inserted into holes to be measured. In addition, the plug gauge allows the gauge portions 11 and 12 to be smoothly inserted into a hole to be measured and can prevent damage on members on the other side to be measured.

The conventional hole plug gauge disclosed in Japanese Patent Laid-Open No. 2001-116502 described above is provided with the air ventilation passages communicating with the insertion leading surface of the gauge portion of the hole plug gauge. This solves the problem that when the gauge portion of the hole plug gauge is inserted into a hole, since there is no escape of air (air ventilation) in the hole and the air is sealed in it when the gauge portion is inserted, it is difficult to smoothly insert the gauge portion, resulting in a lot of trouble in measurement.

Conventionally, forcibly inserting a gauge portion into a hole damages a product or itself, resulting in the occurrence of defective products or making the hole plug gauge unusable. In contrast, the above plug gauge allows smooth insertion of the gauge portion to eliminate the cause of defective products or unusability of the hole plug gauge.

The problem to be solved by the present invention will be described below.

First of all, according to the present invention, a constricted portion and a cylindrical gauge portion having a uniform diameter are extended on one side of a shank portion 1 having a prismatic shape or the like, and a wear checking gauge line or wear checking round point having a predetermined depth and width is formed to extend from one end of the outer circumferential portion of the cylindrical gauge portion with the uniform diameter in the direction of the shank portion. As the gauge portion is repeatedly used to perform positioning and accuracy comparison measurement with respect to slide core pinholes, positioning pinholes, automatic controllers, dedicated devices, jigs and tools, and the like at the time of manufacture of various type of molds for metalworking, the wear checking gauge line or the round point on the outer circumferential surface portion of the gauge portion disappears due to friction. This makes the user accurately recognize the time for maintenance and check the time for replacement of the plug gauge.

In addition, the present invention can reliably and quickly manufacture a wear checking gauge line or wear checking round point extending from an end portion of the outer circumferential surface portion of the gauge portion in the direction of the shank portion while maintaining high accuracy.

Means for Solving the Problem

As a means for solving the problem, the invention defined in claim 1 provides a plug gauge with a maintenance line and a round point in which in a plug gauge body a having a constricted portion 2 formed on one side of a shank portion 1 and a cylindrical gauge portion 3 having a uniform diameter and extending from one side of the constricted portion 2, with the shank portion 1, the constricted portion 2, and the gauge portion 3 being formed axially, a wear checking gauge line 6 having a predetermined depth and a predetermined width is formed to extend from one end portion 8 of an outer circumferential surface portion 7 of the gauge portion 3 in a direction of the constricted portion 2 or a wear checking round point having a predetermined depth and a predetermined diameter is formed at a predetermined position on the outer circumferential surface portion 7 of the cylindrical gauge portion 3.

As a means for solving the problem, the invention defined in claim 2 provides a plug gauge with a maintenance line and a round point in which the wear checking gauge line 6 formed on the outer circumferential surface portion 7 of the cylindrical gauge portion 3 has a linear shape or a wear checking point having a circular shape is formed at a predetermined position on the outer circumferential surface portion 7 of the cylindrical gauge portion 3.

As a means for solving the problem, the invention defined in claim 3 provides a plug gauge with a maintenance line and a round point in which the wear checking gauge line 6 is printed in the outer circumferential surface portion 7 of the cylindrical gauge portion 3 so as to have a depth of 0.3 µm to 0.4 µm and a width of 0.2 mm or the wear checking round point 6a is printed at a predetermined position in the outer circumferential surface portion 7 of the cylindrical gauge portion 3 so as to have a depth of 0.3 µm to 0.4 µm and a diameter of about 2 mm.

As a means for solving the problem, the invention defined in claim 4 provides a plug gauge with a maintenance line and a round point in which the plug gauge body a is formed by using alloy tool steel, a ceramic material, or a superhard material.

As a means for solving the problem, the invention defined in claim provides a method of manufacturing a plug gauge with a maintenance line and a round point, comprising connecting a plug gauge body a having a constricted portion 2 formed on one side of a shank portion 1 and a gauge portion 3 having a uniform diameter and extending from one side of the constricted portion 2, with the shank portion 1, the gauge portion 3, and the constricted portion 2 being formed axially, to a negative electrode base connected to a power supply box c which controls a current, setting a green stencil which has a cut-out portion having a desired marking pattern and from which an electrolytic solution exudes on a carbon filter with the electrolytic solution being contained in a positive electrode handle connected to the power supply box c, energizing the set positive electrode handle while gripping the handle, and forming the wear checking gauge line by performing a marking process by sliding the positive electrode handle from one end portion 8 of the outer circumferential surface portion 7 of the cylindrical gauge portion 3 in a direction of the constricted portion 2 to form a concave shape which has a depth of 0.3 µm to 0.4 µm and a width of 0.2 mm and is blackened, or forming a wear checking round point 6a by performing a marking process without sliding the positive electrode handle to form a concave shape, at a predetermined position on the outer circumferential surface portion 7 of the cylindrical gauge portion 3, which has a depth of 0.3 µm to 0.4 µm and a diameter of about 2 mm and is blackened.

Effects of the Invention

The invention defined in claim 1 provides a plug gauge with a maintenance line and a round point in which in a plug gauge body a having a constricted portion 2 formed on one side of a shank portion 1 and a cylindrical gauge portion 3 having a uniform diameter and extending from one side of the constricted portion 2, with the shank portion 1, the gauge portion 3, and the constricted portion 2 being formed axially, a wear checking gauge line 6 having a predetermined depth is formed to extend from one end portion 8 of an outer circumferential surface portion 7 of the cylindrical gauge portion 3 having a uniform diameter in a direction of the constricted portion 2 or a wear checking round point is formed in a circular shape at a predetermined position on the outer circumferential surface portion 7 of the cylindrical gauge portion 3. Therefore, as compared with conventional plug gauges, this invention has a merit of being capable of reliably and quickly checking the time for maintenance of the plug gauge as the wear checking gauge line or round point formed on the outer circumferential surface portion of the gauge portion of the plug gauge disappears due to friction with the pinholes of test measurement objects.

In addition, the present invention has an excellent merit of contributing to the prevention of defective products, product making with higher accuracy, and the like by forming the wear checking gauge line or round point.

The invention defined in claim 2 provides a plug gauge with a maintenance line and a round point in which the wear checking gauge line 6 formed on the outer circumferential surface portion 7 of the cylindrical gauge portion 3 having a uniform diameter has a linear shape. This invention has the same effects as those of the invention defined in claim 1.

The invention defined in claim 3 provides a plug gauge with a maintenance line and a round point in which the wear checking gauge line 6 is printed in the outer circumferential surface portion 7 of the cylindrical gauge portion 3 so as to have a depth of 0.3 µm to 0.4 µm and a width of 0.2 mm or the wear checking round point 6a is printed at a predetermined position in the outer circumferential surface portion 7 of the cylindrical gauge portion 3 so as to have a depth of 0.3 µm to 0.4 µm and a diameter of about 2 mm. This invention has the same effects as those of the invention defined in claim 1.

The invention defined in claim 4 provides a plug gauge with a maintenance line and a round point in which the plug gauge body a is formed by using alloy tool steel, a ceramic material, or a superhard material. This invention has the same effects as those of the invention defined in claim 1.

The invention defined in claim 5 provides a method of manufacturing a plug gauge with a maintenance line and a round point, comprising connecting a plug gauge body a having a constricted portion 2 formed on one side of shank portion 1 and a cylindrical gauge portion 3 having a uniform diameter and extending from one side of the constricted portion 2, with the shank portion 1, the gauge portion 3, and the constricted portion 2 being formed axially, to a negative electrode base connected to a power supply box c which controls a current, setting a green stencil which has a cut-out portion having a desired marking pattern and from which an electrolytic solution exudes on a carbon filter with the electrolytic solution being contained in a positive electrode handle connected to the power supply box c, energizing the set positive electrode handle while gripping the handle, and forming the wear checking gauge line by performing a marking process by sliding the positive electrode handle from one end portion 8 of the outer circumferential surface portion 7 of the cylindrical gauge portion 3 in a direction of the constricted portion 2 to form a concave shape which has a depth of 0.3 µm to 0.4 µm and a width of 0.2 mm and is blackened, or forming a wear checking round point by performing a marking process without sliding the positive electrode handle to form a concave shape, at a predetermined position on the outer circumferential surface portion 7 of the cylindrical gauge portion 3, which has a depth of 0.3 µm to 0.4 µm and a diameter of about 2 mm and is blackened. Therefore, this invention has a merit of being capable of manufacturing a plug gauge which allows the user to easily check wear concerning diameter accuracy as the wear checking gauge line or round point 6a wears out and to directly perform quality control with high accuracy.

BEST MODE FOR CARRYING OUT THE INVENTION

The modes for carrying out the inventions defined in claims 1 to 5 of the present invention are common, and hence will be collectively described below.

Referring to the accompanying drawings, reference symbol a denotes a plug gauge body which forms a plug gauge with a maintenance line and a round point according to the present invention and has the following arrangement.

The plug gauge body a is formed by using alloy tool steel, a ceramic material, a superhard material, or the like.

Reference numeral 1 denotes shank portion having a predetermined length and a prismatic shape (a hexagonal prismatic shape in general).

On the left and right two sides of the prismatic shank portion 1, a constricted portion 2 is formed on one end portion coaxially with the prismatic shank portion 1, and a cylindrical gauge portion 3 having a predetermined length and a uniform diameter is formed by extending the left end portion of the constricted portion 2.

In addition, a constricted portion 4 is formed on the other end portion of the prismatic shank portion 1, and a cylindrical gauge portion 5 having a predetermined length and a uniform diameter is formed by extending the right end portion of the constricted portion 4.

Figure 1:
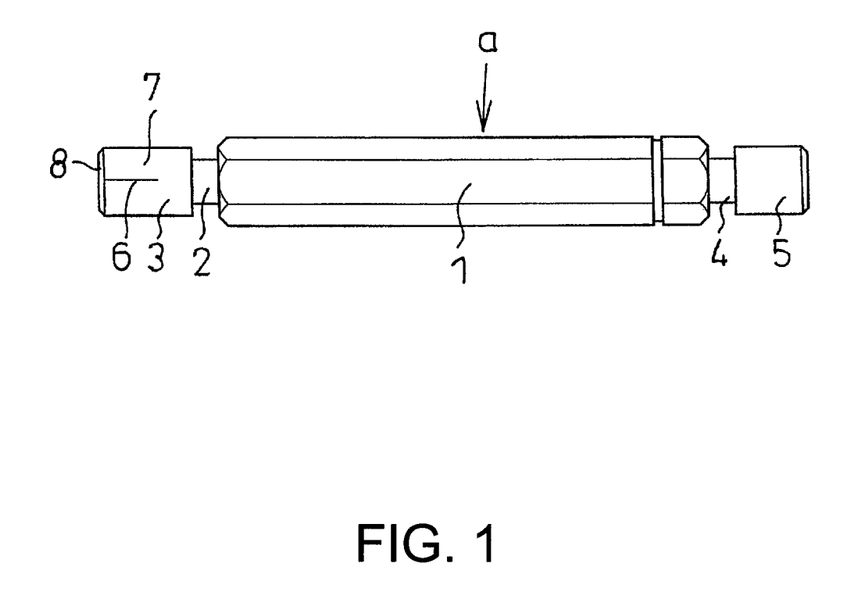
FIG. 1 is a front view showing a plug gauge with a maintenance line and a round point and a method of manufacturing the same according to the present invention.
Figure 2:
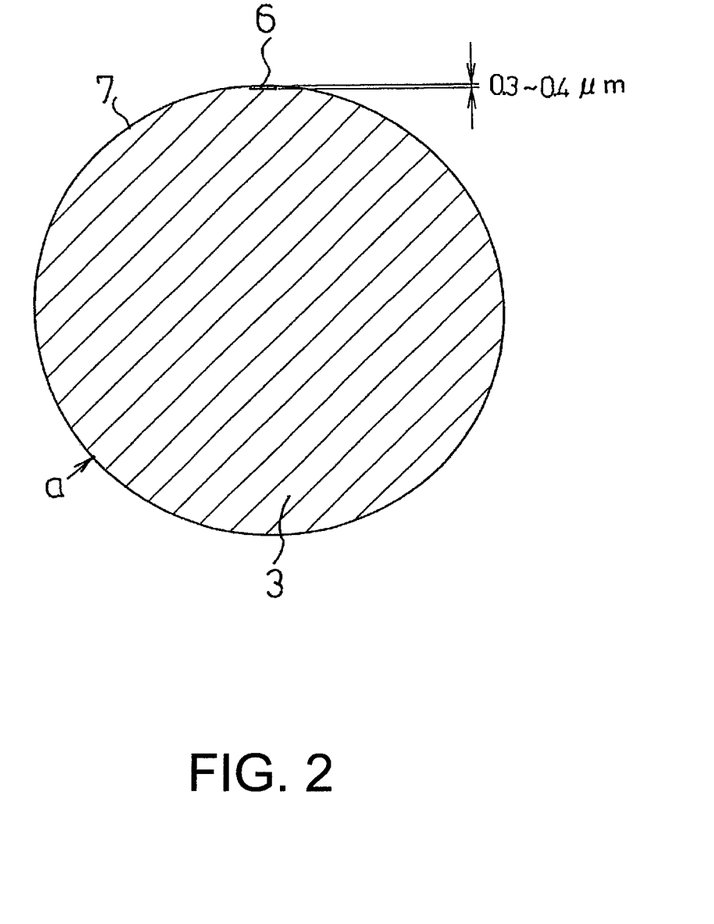
FIG. 2 is an enlarged longitudinal sectional view of a gauge portion of the plug gauge.

The prismatic shank portion 1 formed in the above manner, the constricted portions 2 and 4, the gauge portion 3, and the cylindrical gauge portion 5 are coaxially formed (FIG. 1).

With reference to the accompanying drawings, reference numeral 6 denotes a wear checking gauge line with a predetermined depth of 0.3 μm to 0.4 μm and a width of 0.2 mm, which extends from one end portion 8 of an outer circumferential surface portion 7 of the cylindrical gauge portion 3 with the uniform diameter in the direction of the cylindrical constricted portion 2 with the uniform diameter.

The wear checking gauge line 6 formed on the outer circumferential surface portion 7 of the cylindrical gauge portion 3 with the uniform diameter has a linear shape.

Reference numeral 6a denotes a round point formed in the outer circumferential surface portion 7 of the cylindrical gauge portion 3 at a predetermined position by printing so as to have a depth of 0.3 μm to 0.4 μm and a diameter of about 2 mm.

In addition, the wear checking gauge line 6 having the predetermined depth and a width of 0.2 mm is printed in the outer circumferential surface portion 7 of the cylindrical gauge portion 3 with the uniform diameter by a marking process (to be described below).

Figure 6:
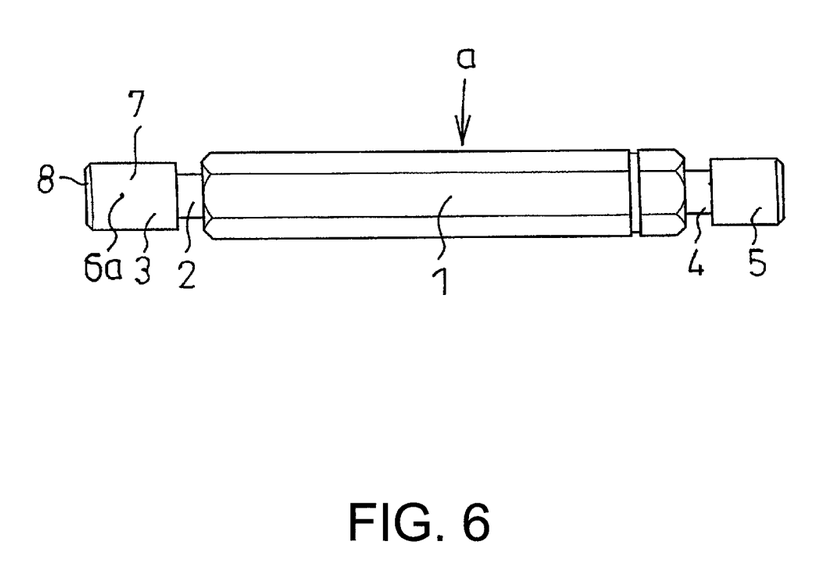
FIG. 6 is a front view of a plug gauge according to the second embodiment.

In the marking process method for the wear checking gauge line 6, the wear checking gauge line is printed by using the electrolytic marking apparatus shown, in particular, in FIG. 6 (a perspective view of the electrolytic marking apparatus used in a manufacturing process for a pin gauge) disclosed in Japanese Patent No. 5035735 ("PIN GAUGE WITH WEAR CHECKING LINE AND METHOD OF MANUFACTURING THE SAME") which was applied by the present applicant on Jun. 13, 2011 and has been granted.

Figure 5:
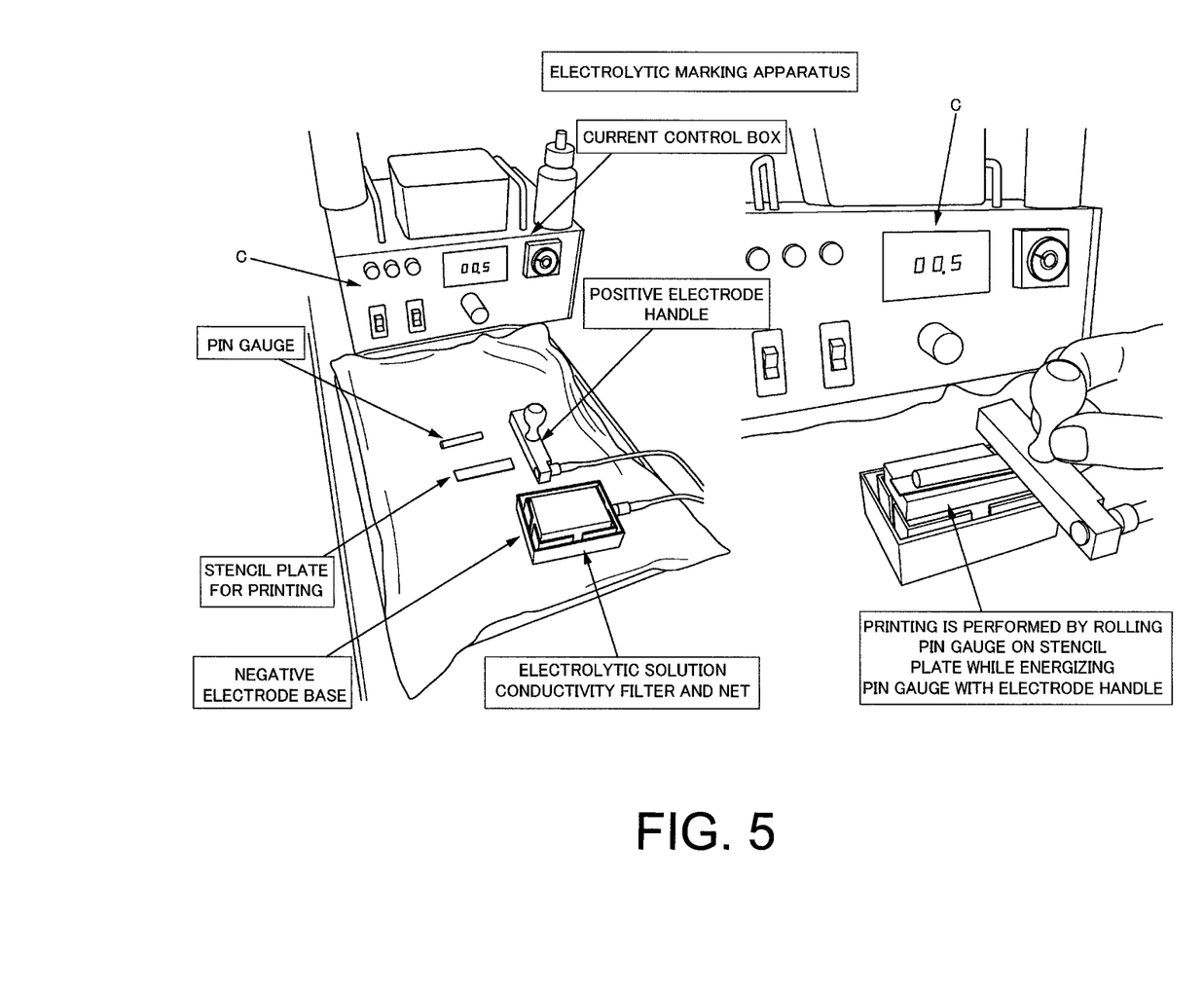
FIG. 5 is a perspective view of a power supply box and the like which manufacture the plug gauge with the maintenance line and the round point in FIG. 1.

That is, referring to FIG. 6, in the present invention, the plug gauge body a is connected to a negative electrode base connected to a power supply control box c shown in FIG. 5. A green stencil which has a cut-out portion having a desired marking pattern and from which an electrolytic solution exudes is then set on a carbon filter with the electrolytic solution being contained in a positive electrode handle connected to the power supply box b.

While the user grips the positive electrode handle set in the above manner, the handle is energized and slid on the outer circumferential surface portion 7 of the gauge portion 3 of the plug gauge body a from one end portion 8 in the direction of the constricted portion 2.

A marking process is performed by sliding the positive electrode handle in the above manner to form the wear checking gauge line 6 having a depth of 0.3 μm to 0.4 μm and a width of 0.2 mm by forming a concave shape in the outer circumferential surface portion 7 of the gauge portion 3 by corrosion and blackening the line.

The following is a description of a printing process step for the wear checking gauge line 6 on the plug gauge body a according to the present invention.

In the marking process method for the wear checking round point 6a, the wear checking round point is printed by using the electrolytic marking apparatus shown, in particular, in FIG. 6 (a perspective view of the electrolytic marking apparatus used in a manufacturing process for a pin gauge) disclosed in Japanese Patent No. 5035735 ("PIN GAUGE WITH WEAR CHECKING LINE AND METHOD OF MANUFACTURING THE SAME") which was applied by the present applicant on Jun. 13, 2011 and has been granted.

That is, referring to FIG. 6, in the present invention, the plug gauge body a is set on a negative electrode base connected to a power supply control box c shown in FIG. 5. A green stencil which has a cut-out portion having a desired marking pattern and from which an electrolytic solution exudes is then set on a carbon filter with the electrolytic solution being contained in a positive electrode handle connected to the power supply box b.

While the user grips the positive electrode handle set in the above manner, the handle is energized. The user then brings the positive electrode handle into contact with the outer circumferential surface portion 7 of the gauge portion 3 of the plug gauge body a for a predetermined period of time, e.g., about 2 sec. As a result, a marking process is performed to form the wear checking round point 6a having a depth of 0.3 μm to 0.4 μm and a diameter of about 2 mm in a concave shape in the outer circumferential surface portion 7 of the gauge portion 3 by corrosion and blacken the point.

A printing process step for the wear checking round point 6a on the plug gauge body a according to the present invention has been described above.

The operation of the plug gauge according to the present invention is executed in the above manner.

Figure 3:
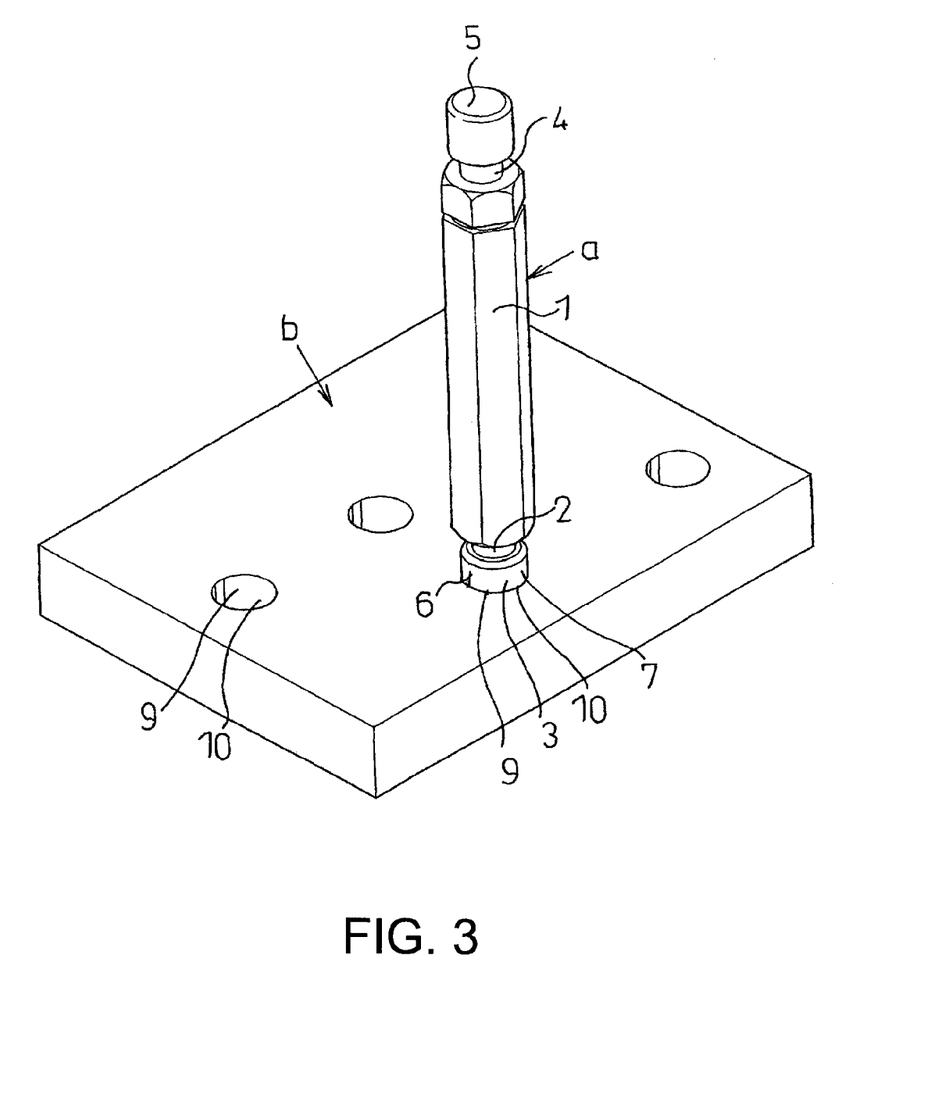
FIG. 3 is a perspective view showing the gauge state of the gauge portion of the plug gauge.
Figure 4:
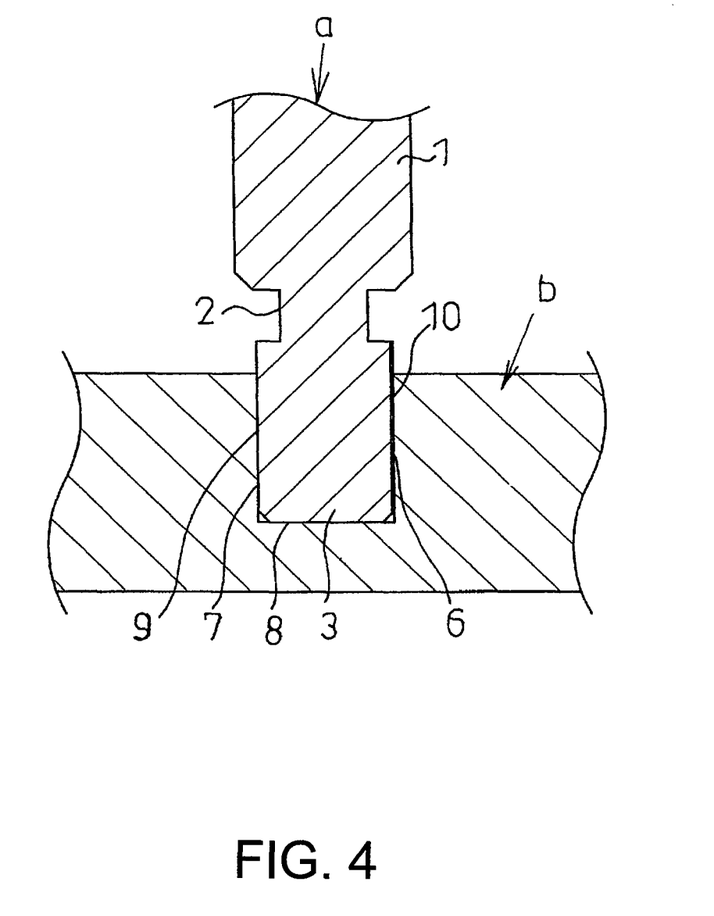
FIG. 4 is a partially cutaway enlarged longitudinal sectional view showing the gauge state of the gauge portion of the plug gauge.

The user inserts the gauge portion 3 of the plug gauge into a hole 9 of a test measurement object b to perform gauging operation. At this time, a circumferential surface portion 10 of the hole 9 comes into slidable contact with the outer circumferential surface portion 7 of the cylindrical gauge portion 3.

As described above, as the user repeats slidable contact operation with respect to the gauge portion 3, the outer circumferential surface portion 7, and the circumferential surface portion 10 of the hole 9, the wear checking gauge line 6 or round point 6a having a depth of 0.3 μm to 0.4 μm and a width of about 0.2 mm, printed on the outer circumferential surface portion 7 of the gauge portion 3, keeps gradually wearing.

As described above, as the wear checking gauge line 6 or round point 6a wears out, the user can easily and reliably check wear concerning diameter accuracy. In addition, checking wear of the gauge line 6 or round point 6a makes it possible to directly perform quality control with high accuracy.

Note that printing on a ceramic material is performed by a special printing method such as laser marking.

REFERENCE SIGNS LIST a plug gauge body
b test measurement object
1 shank portion
2 constricted portion
3 gauge portion
4 constricted portion
5 cylindrical gauge portion
6 wear checking gauge line
6a wear checking round point
7 outer circumferential surface portion
8 one end portion
9 hole
10 circumferential surface portion

What is claimed is:

1. A plug gauge with a maintenance line and a round point, comprises:
    a plug gauge body having a constricted portion formed on one side of a shank portion and a cylindrical gauge portion having a uniform diameter and extending from one side of the constricted portion, the shank portion, the cylindrical gauge portion, and the constricted portion being formed axially;
    a wear checking gauge line having a predetermined depth and a predetermined width formed to extend from one end portion of an outer circumferential surface portion of the cylindrical gauge portion in a direction of the constricted portion, or a wear checking round point formed at a predetermined position on the outer circumferential surface portion of the cylindrical gauge portion.

2. The plug gauge with the maintenance line and the round point according to claim 1, wherein the wear checking gauge line formed on the outer circumferential surface portion of the cylindrical gauge portion has a linear shape or the wear checking point formed at a predetermined position on the outer circumferential surface portion of the cylindrical gauge portion has a circular shape.

3. The plug gauge with the maintenance line and the round point according to claim 2, wherein the wear checking gauge line is printed in the outer circumferential surface portion of the cylindrical gauge portion so as to have a depth of 0.3 μm to 0.4 μm and a width of 0.2 mm, or printed at a predetermined position in the outer circumferential surface portion of the cylindrical gauge portion so as to have a depth of 0.3 μm to 0.4 μm and a diameter of 2 mm.

4. The plug gauge with the maintenance line and the round point according to claim 3, wherein the plug gauge body is formed by using alloy tool steel, a ceramic material, or a superhard material.

5. The plug gauge with the maintenance line and the round point according to claim 2, wherein the plug gauge body is formed by using alloy tool steel, a ceramic material, or a superhard material.

6. The plug gauge with the maintenance line and the round point according to claim 1, wherein the wear checking gauge line is printed in the outer circumferential surface portion of the cylindrical gauge portion so as to have a depth of 0.3 μm to 0.4 μm and a width of 0.2 mm, or printed at a predetermined position in the outer circumferential surface portion of the cylindrical gauge portion so as to have a depth of 0.3 μm to 0.4 μm and a diameter of 2 mm.

7. The plug gauge with the maintenance line and the round point according to claim 6, wherein the plug gauge body is formed by using alloy tool steel, a ceramic material, or a superhard material.

8. The plug gauge with the maintenance line and the round point according to claim 1, wherein the plug gauge body is formed by using alloy tool steel, a ceramic material, or a superhard material.

* * * * *